United States Patent [19]

Mason et al.

[11] Patent Number: 4,850,877
[45] Date of Patent: Jul. 25, 1989

[54] METHOD OF DETERMINING STRESS EFFECTS IN COMPONENTS OF THE HUMAN KNEE AND ANTHROPOMORPHIC LEG DEVICE THEREFOR

[75] Inventors: Jeffery T. Mason, Escondido; Patrick W. Cawley, San Diego; Bradley R. Mason, Carlsbad, all of Calif.

[73] Assignee: Donjoy, Inc., Carlsbad, Calif.

[21] Appl. No.: 5,415

[22] Filed: Jan. 20, 1987

[51] Int. Cl.[4] ............................................. G09B 23/32
[52] U.S. Cl. .................................................... 434/274
[58] Field of Search .............. 434/267, 274, 275, 265; 73/866.4; 623/30, 31, 32, 13, 39, 47, 59

[56] References Cited

U.S. PATENT DOCUMENTS

| 2,046,069 | 6/1936 | Greissinger | 623/46 |
|---|---|---|---|
| 2,472,819 | 6/1949 | Geisen | 623/57 |
| 3,196,463 | 7/1965 | Farneth | 623/49 |
| 3,557,471 | 1/1971 | Payne et al. | 434/274 |
| 3,664,038 | 5/1972 | Searle et al. | 434/274 |
| 3,740,871 | 6/1973 | Berton et al. | 434/267 |
| 3,755,920 | 9/1973 | Smrcka | 434/274 |
| 3,841,163 | 10/1974 | Daniel | 73/172 |
| 3,895,451 | 7/1975 | Smrcka | 434/274 |
| 3,962,801 | 6/1976 | Gonzalez | 434/274 |
| 4,000,564 | 1/1977 | Haffner et al. | 434/274 |
| 4,235,025 | 11/1980 | Kortge | 434/274 |
| 4,261,113 | 4/1981 | Alderson | 434/274 |
| 4,276,032 | 6/1981 | Woley et al. | 434/274 |
| 4,301,551 | 11/1981 | Dore et al. | 623/13 |
| 4,349,339 | 9/1982 | Daniel | 434/274 |
| 4,466,800 | 8/1984 | Breiden | 434/267 |
| 4,488,433 | 12/1984 | Denton | 73/432 R |
| 4,605,373 | 8/1986 | Rosen | 434/274 |
| 4,701,132 | 10/1987 | Groesch | 434/274 |
| 4,744,793 | 5/1988 | Parr et al. | 623/13 |

Primary Examiner—Richard J. Apley
Assistant Examiner—H. Flaxman
Attorney, Agent, or Firm—Dressler, Goldsmith

[57] ABSTRACT

A method is described for obtaining quantitative data on the response of individual components of a human knee to external stresses which comprises having an anthropomorphic knee device which includes individual component means for simulating at least one principal component of the knee and load determining means which after calibration are used to determine the effect on the equivalent component in a human knee joint resulting from that external stress. Also described in an anthropomorphic leg device for performing the method in which cables represent the principal components of the knee and are operably connected to load cells so that the stresses imparted to each of the principal components by a traumatic impact can be individually measured and assessed. Measurements with this invention are found to correlate closely to the stresses in the respective components, such as ligaments and muscle groups, of the human knee. The invention is thus ideally suited for analyzing knee injuries, for teaching medical and emergency personnel to identify various types of knee injuries and for testing of knee braces and other orthopedic devices.

26 Claims, 3 Drawing Sheets (ANTERIOR VIEW)

(LATERAL VIEW)

(ANTERIOR VIEW)

ANTERIOR VIEW

POSTERIOR VIEW

METHOD OF DETERMINING STRESS EFFECTS IN COMPONENTS OF THE HUMAN KNEE AND ANTHROPOMORPHIC LEG DEVICE THEREFOR

FIELD OF THE INVENTION

The invention herein relates to methods of measuring and analyzing knee stress responses and to anthropomorphic testing and teaching devices for use in such methods.

BACKGROUND OF THE INVENTION

It has long been considered that the human knee is particularly susceptible to sudden and debilitating injury. The knee structure is complex and has little resistance to external forces applied from nonaxial directions. Further, the knee is frequently unable to move effectively to absorb such nonaxial forces, since placing of the foot fixes the distal end of the leg and effectively converts the leg into a rigid beam with the knee as the "weak spot".

In addition, the activities that many people engage in frequently expose the knee to external forces under conditions where the knee is already under stress, thus increasing the severity of injuries. It is unfortunately common for severe knee injuries to be incurred by those who participate in sports such as football, skiing and soccer, where the legs are subject to a highly stressed environment. Such injuries are often sufficiently severe that extensive reconstructive surgery is required. Even with surgery it is not uncommon for these injuries to force the end of an athlete's career or to limit the ability of the injured person again to participate in recreational athletics. In addition, a knee injury even for a non-athlete can result in permanent limitation of knee function and a greater or lesser degree of impairment of the person's leg function.

The knee is a complex joint, so there are several components which are of major importance in assessing injuries of the knee; these will be described in detail below in connection with FIGS. 1 and 2. Because one or more of these components may be hyperextended, dislocated or severed a variety of different knee injuries resulting from traumas or other applied forces are possible. While there have been efforts in the past to analyze the response of the knee to such forces, it has only been possible to determine gross response for the knee as a whole; analysis of the response of individual components on a quantitative basis could not be performed. There have been attempts to simulate knees with anthropomorphic leg devices, but these prior art devices have not been capable of determining the individual stresses that each of the knee-related components, such as ligaments and muscle groups, is subject to under a particular strength and direction of force. The prior art devices have essentially all treated the knee as a simple unitary hinged joint for which the external axial loading has been measured, but no device has had the capability of determining the internal effects resulting from the external forces. In a few cases, such as the device shown in U.S. Pat. No. 4,349,339, provision has been made for measurement of forces in three dimensions. However, such a device is still capable only of measuring gross external shearing forces in three dimensions since the knee is still treated as a simple hinge. Thus while one can determine lateral or anterior/posterior externally applied forces, the prior art devices cannot provide any information with respect to the effects of such forces on the individual components of the knee or of the type and severity of the knee injury which would occur under such forces.

It would be particularly advantageous to be able to make reproducible and quantitative studies of the responses of individual knee components to external stresses, and to have a device which would be capable of accurately determining such responses of the individual principal components of the knee when the knee as a whole suffers externally applied forces, such as a blow or similar trauma. Such information would, for instance, allow the design of knee braces and other orthopedic devices which would maximize the amount of protection available for the types of traumas most likely to be encountered in sports. Similarly, with such information physicians would be able to predict the most likely type of injuries to be sustained under defined external circumstances and therefore be able to evaluate actual knee injuries more quickly and efficiently. Equipment designers, such as automobile designers, could also design their products so as to minimize the possibility of the equipment causing major trauma to persons' knees in a collision or other accident.

It would also be advantageous to have a method and device for use in teaching and study which would give accurate and reproducible data on the pathology of the knee. This would be valuable for general medical training as well as to familiarize emergency medical and physical training people with knee injuries and disorders.

Finally, it would be valuable to have a method and device for obtaining consistent and reproducible quantitative data on the knee and its components, so that knee testing instruments and orthopedic devices could be evaluated against consistent quantitative standards.

BRIEF SUMMARY OF THE INVENTION

In one aspect the invention herein is method for obtaining quantitative data on the response of individual components related to a human knee to externally applied forces affecting the knee, which comprises:

a. having an anthropomorphic device which comprises bone member means for simulating the configuration of the actual femur, tibia and fibula of a human leg; component means cooperating with the bone means for simulating at least one principal component related to the knee; and load determining means attached to the component means;

b. calibrating each of the load determining means to simulate predetermined stiffness characteristics of the human knee;

c. determining from each applicable load determining means the quantitative response of the component means when the anthropomorphic device is subjected to externally applied force; and d. determining from the response the effect on the equivalent component in a human knee joint resulting from the force.

In another aspect, the invention is an anthropomorphic device simulating the human leg from which quantitative responses of human knee components to externally applied loads can be obtained, which comprises:

a. at least two rigid bone members, the first having the general shape of the distal end of the human femur and the second having the general shape of the proximal ends of the human tibia and fibula, the bone members being aligned endwise in the configuration of the actual femus, tibia and fibula of a person's knee and together simulating a human knee;

b. a plurality of cooperating pairs of cables and sheaths, each cable representing a principal component related to the knee and being slidably encased in the cooperating sheath for a portion of its length, with one end of each cable and sheath pair being operably attached to a load cell, the end of each cable distal to the load cell extending outwardly from the distal end of the sheath;

c. The distal end of the sheath being secured to the first bone member at a point such that the cooperating cable exits from said first bone member at a point equivalent to where the component, which the cable represents, would be attached or adjacent to the femur, and the distal end of the cable being fixed to the second bone member at a point where the component would be attached to the tibia or fibula;

d. means for calibrating the tension/elongation characteristics in each of the cable and sheath pairs to simulate predetermined stiffness and displacement characteristics of the human knee;

e. means for calibrating each of the cable and sheath pairs to simulate predetermined resting tension characteristics of the applicable individual component related to the human knee; and f. means for determining from each load cell the differential tension imposed on the cable when the simulated knee is subjected to external traumatic force, with the differential tension being related to stress in said component in a human knee joint resulting from said force and from which accurate analysis of the response of said component of the knee to such force can be obtained.

The principal components related to the knee which may be studied with this invention are the anterior cruciate ligament, the posterior cruciate ligament, the medial collateral ligament, the lateral collateral ligament, the hamstring muscles, the quadriceps muscles, the patella and the menisci. Any one of these can be studied separately, or, alternatively, all or a plurality of these components cam be represented simultaneously and the user of the device can obtain stress data on each of the represented components during a single test.

DETAILED DESCRIPTION AND PREFERRED EMBODIMENTS

Figure 1:
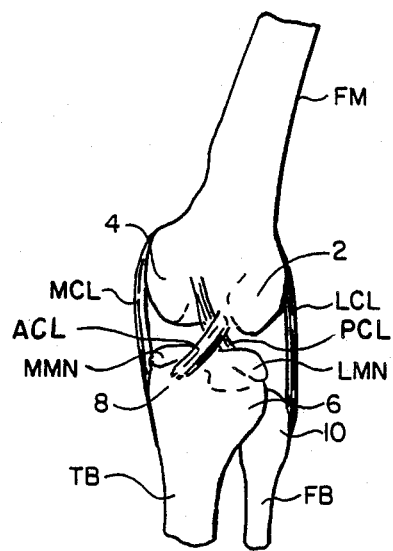
FIG. 1 is a schematic anterior view of the human knee indicating the four principal ligaments of interest, with the bones shown spaced apart so that the directions in which the ligaments run can be illustrated.
Figure 2:
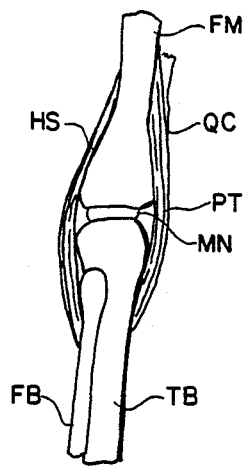
FIG. 2 is a schematic lateral view of the human knee illustrating the general position of the muscle groups of interest, the patella and the menisci.

The invention herein in its method and apparatus aspects is best understood by first considering the structure of an actual human knee as illustrated schematically in FIGS. 1 and 2. The bone of the upper leg is the femur FM. The distal end of the femur is expanded to form the lateral condyle 2 and the medial condyle 4. Distal to the femur in the lower leg are the tibia TB and fibula FB which terminate at their proximate ends in the medial and lateral condyles 8 and 6 of the tibia and the head 10 of the fibula. (In FIG. 1 the bones are shown substantially spaced apart so that the ligaments can be more clearly illustrated. Actually, and with the device of this invention, they are quite closely adjacent and separated by the medial and lateral menisci, as shown in FIG. 2.)

The two central ligaments of the knee are the anterior cruciate ligament ACL and the posterior cruciate ligament PCL. The ACL passes from the posterior intercondylar notch of the femur to the anterior intercondylar area of the proximal end of the tibia. Its principal function is to prevent backward (posterior) sliding of the femur and hyperextension of the knee and to limit medial rotation of the femur when the foot is on the ground and fixed. The PCL passes from the anterior face of the intercondylar notch of the distal end of the femur to the posterior intercondylar area of the proximal end of the tibia. Its principal function is to prevent forward sliding of the femur, particularly when the knee is flexed.

The two principal lateral ligaments of the knee are the lateral collateral ligament LCL and the medial collateral ligament MCL. The MCL runs from the medial epicondyle of the distal end of the femur to the medial side of the tibial plateau (and is, therefore sometimes referred to as the tibial collateral ligament). The LCL runs from the lateral epicondyle at the distal end of the femur to the lateral side of the head of the fibula (and is, therefore, sometimes referred as the fibular collateral ligament). The collateral ligaments function to prevent lateral or medial angulation of the knee joint.

FIG. 1 also shows the lateral meniscus LMN and the medial meniscus MMN in their correct relationship to the tibia but spaced apart from the femur. In fact they are in contact with both bones and serve to cushion them.

In FIG 2 the two principal groups of muscles related to the knee are schematically illustrated, as in the patella (kneecap) PT. These muscles ar the quadriceps QC and the hamstrings HS. While these muscle groups are complex, for the purposes of this invention they may each often be considered to be unitary and respectively the anterior and posterior muscles of the knee, to be represented in the anthropomorphic device each as a single component. Alternative, by use of additional cables the various individual muscles within the groups can be separately represented. The quadriceps muscles are the rectus femoris, the vastus medialis, the vastus lateralis and the vastus intermedius; the hamstrings are the biceps femoris, the semitendinosus and the semimembranosus.

In knee injuries any one or more of these components may be hyperextended, severed, dislocated or torn. There may be tears in a ligament or muscle itself or at its point of attachment to a bone. The patella may be broken or dislocated. The menisci may be dislocated or torn. It will be apparent that the particular type of injury which may be incurred will be dependent upon the direction from which the external force is applied, the strength of the force and the degree to which the knee (and leg) can dissipate or absorb the force. Further, since each of the components will respond individually to the force, there may be no adverse effect on some components, slight injury to others and severe injury to still others. It has not previously been possible to differentiate such effects in anthropomorphic devices so that the devices could be used for medical analysis, teaching or orthopedic equipment design, since prior art devices did not attempt to duplicate the complex knee structure but simply treated the knee as a simple unitary hinged joint.

It is recognized that there are other components of the knee, such as the popliteus tendon, the coronary ligament and the patellar tendon, which can be affected by trauma to the knee. These can also be represented in the device of this invention by suitable cables. It has been found in medical practice, however, that most knee problems and injuries involve the principal components described herein, and therefore the elements of the device of this invention are primarily directed toward representing those components. The contribution to knee injuries and problems by the other knee components are for the most part minor and can be disregarded in using the present device to study and evaluate traumatic effects on knees.

The invention as a whole is best explained by considering it in relation to the structure of a preferred anthropomorphic device useful for practice of the method, which is illustrated in FIGS. 3–8. The principal components related to the knee are effectively represented individually in the device, in contrast to prior art devices which considered the knee as a single unitary joint. The principal structural elements of the device are the femoral bone member 12, the tibial bone member 14 and the fibular bone member 15, which are supported by foot structure 16 and surmounted by load cell structure 18. (In an alternative, less preferred structure not shown, the fibular bone member 15 could be eliminated and the tibial bone member 14 could approximate a composite of the human tibia and fibula, since in the human knee the two lower limb bones generally act as a unit. However, the preferred embodiment is that shown with both bone members 14 and 15 to more closely simulate an actual knee.) In this device the femoral bone member 12 is aligned with the tibial bone member 14 and fibular bone member 15 at a small angle (about 20°) representing the leg with a slight amount of flexion. This angle is not critical, however, and can be set at any angle (generally 0° to 90°) depending on the particular configuration (e.g., sitting, standing, running) which it is desired to examine. The distal end of the femoral bone member 12 and the proximal ends of the tibial bone member 14 and fibular bone member 15 (using the spacial relationship terms equivalent to a human leg) are closely adjacent and separated by free floating pads 20 which are made of rubber, plastic or a similar material which is reasonably firm but resilient and effectively represents physical characteristic of the menisci.

Load cell structure 18 has a shallow box-like frame 22 which in the embodiment shown has three load cells placed at either end 24 and 26. The particular layout and orientation of the load cell structure is not critical, as long as the cables can move with little frictional resistance. The embodiment shown was selected since it minimizes the bending required of the cables and sheaths. It will also be understood that the load cell structure could be mounted at a different angle or perhaps even mounted on a separate support such as an adjacent wall or rack. There is also a bottom plate 30 covering the underside of the load cell structure 18. The size of the structure 18 is chosen to accommodate the number of load cells which are used; in the embodiment illustrated in FIGS. 3–8 there are six load cells, one for each of the four principal ligaments and one for each of the two principal muscle groups. For convenience, each of these cells may be labeled as to the component it relates to, as illustrated by the abbreviations 32 on the front surface of each 24. The load cells may be custom designed or commercially obtained; the principal requirements are they be small enough to fit in the structure and capable of reading accurately over the desired stress measurement range (at lest a range of 0–2000 N, preferably 0–4000 N). Each of the load cells 34 is mounted in the load cell structure 18 by means of a threaded rod 36 which is passed with slight clearance through a hole in the end 24 of structure 22. The rod 36 extends outwardly from the end 24 and has fitted thereon a compression spring 38, a washer 40 and an adjusting nut 42 (whose function will be described below).

Attached to the opposite end of each load cell 34 is a cable 44, each of which represents a different ligament or muscle group. Typically these ar stranded steel cables having an outside diameter no greater than the bundle diameter of the ligament or muscle group represented. Usually this will result in a diameter in the range of from 1/16 to 3/16 in. (1.6 to 4.8 mm), preferably about 3/32 in. (2.4 mm). The particular material from which the cables are made is not critical, as long as the elongation and other physical properties of the cable material are known and are consistently reproducible, so that such properties can be allowed for in calibrating the device. Their movement under impact must also be reproducible and accurately reflect the stresses imparted by the impact. We have found that 3/32 in. (2.4 mm) diameter 7×19-stranded stainless steel cable is quite satisfactory.

Each cable 44 is threaded through a hollow tube or sheath 46 which is preferably rigid and of metal and which is butted against the underside of bottom plate 30 at 48, with the cable being guided around a pulley 45 (which rotates on shaft 43) and passed downwardly through hole 47 in the bottom 30 of structure 22. (If the sheath is not of metal or other rigid material it must be stiff enough to be secured at each end without collapsing.) It may also be desirable to cover each cable 44 with a low friction wrap or coating such as a polytetrafluoroethylene film or sleeve (not shown) to reduce friction as the cable 44 moves within the sheath 46.

Each of the sheathed cables runs axially down the outside of femoral bone member 12. (If the sheathed cables are not rigid they may conveniently be held in place by cable ties.) As the sheathed cables approach the distal end of femoral bone member 12 they diverge to be secured in the appropriate places to represent the defined ligaments and muscles. For brevity in this description, the operation of the cables will be described only with respect to a single example. However, it will be understood that all of the cables operate in the same manner. In the drawings each of the cables and the muscle group or ligament which each represents can be identified according to the following letter suffixes for the defined components:

| Suffix | Represents |
|---|---|
| a | Quadriceps muscle group |
| b | Lateral collateral ligament |
| c | Posterior cruciate ligament |
| d | Anterior cruciate ligament |
| e | Medial collateral ligament |
| f | Hamstrings muscle group |

Figure 7:
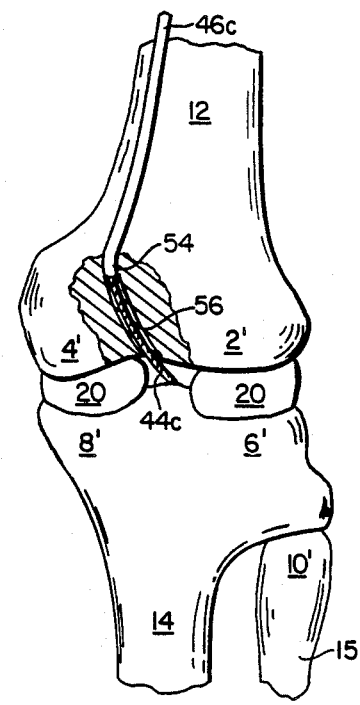
FIG. 7 is an anterior view, partially cut away, of the knee joint of this device showing the routing of the posterior cruciate ligament cable.
Figure 4:
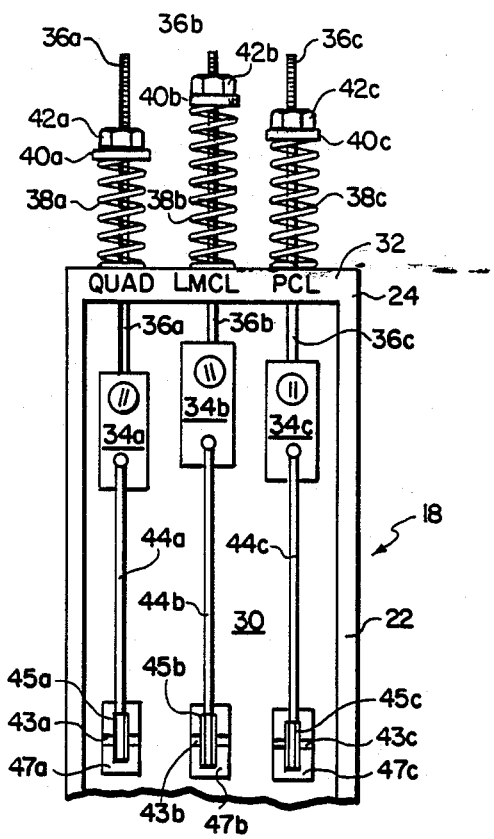
FIG. 4 is a frontal view of a load cell element of the device.
Figures 5, 6:
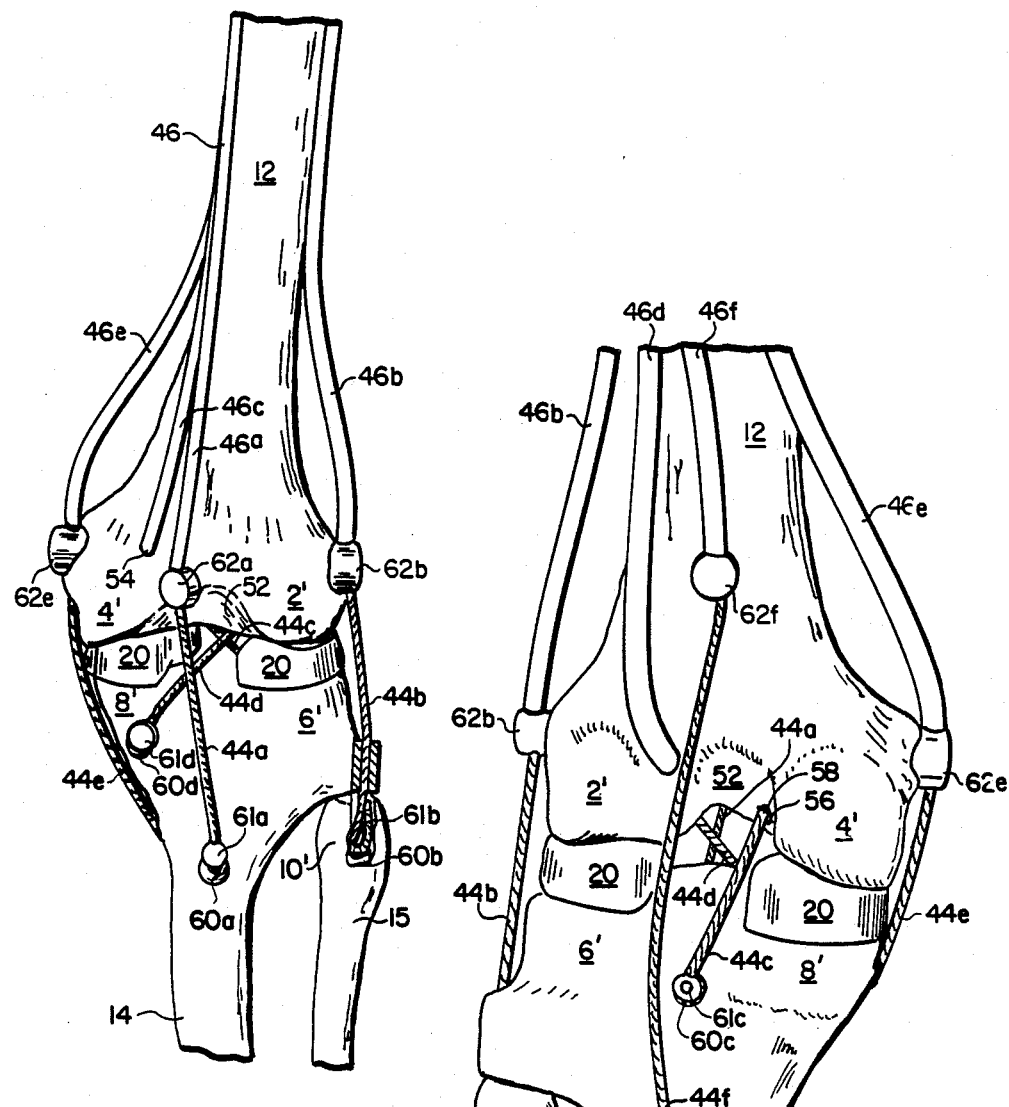
FIG. 5 is an anterior view of the knee joint of the device.
FIG. 6 is a posterior view of the knee joint of the device.

Further, in the detailed structure shown in FIGS. 5-7 the simulated parts of the knee bones such as the condyles are represented by the same numbers respectively as in FIG. 1 for the natural elements but with a prime symbol appended. It will be seen from FIGS. 5 and 6 that the bone configurations have been faithfully represented as far as function is concerned.

The operation of the cables will be described generally by reference to the cable representing the PCL, i.e., cable 44c with sheath 46c. The sheathed cable 44c/46c runs down the femoral bone member 12 and diverges anteriorly, turning back posteriorly to encounter the anterior femoral surface at the edge of the medial condyle 4' adjacent the intercondylar notch 52 at point 54. At this point (as shown in section in FIG. 7) a hole 56 is drilled through the femoral bone member 12 so that the PCL cable 44c emerges from the intercondylar notch 52 at the proper location to represented the point of attachment of the actual PCL to the femur. The hole 56 is of a diameter such that the cable 44c passes freely and with slight clearance through it but the sheath 46c is butted against the shoulder formed at point 54 by the surface of the member 12. In other words, the diameter of hole 56 is sufficiently large to pass cable 44c but smaller than the diameter of sheath 46c such that sheath 46c is secured against the surface of member 12. Sheath 46c is, therefore, fixed at both ends against movement by base 26 of load cell structure 18 and the surface of member 12 at point 54. Cable 44c, however, can move freely through sheath 46c and hole 56.

Where cable 44c emerges from hole 56 at point 58 it is angled in the proper orientation to represent the PCL and passes through the intercondylar notch to be secured near to the medial condyle area 8' of the posterior end of tibial member 14. In the embodiment shown the cable ends in ball 61c and is secured by seating ball 61c in socket 60c. Alternatively the end of the cable could be secured to the bone member by being attached with a screw or a screw post.

Figure 3:
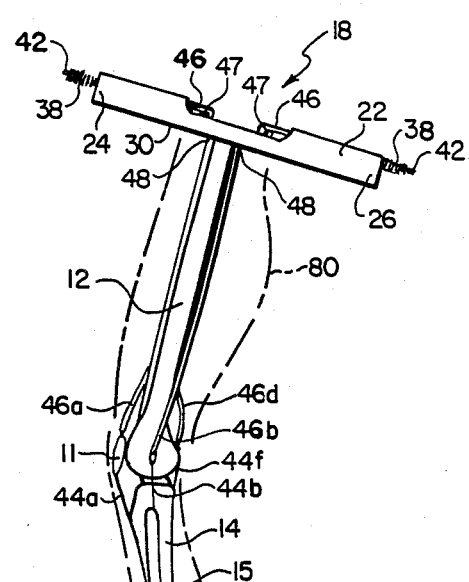
FIG. 3 is a side view of the device of this invention.

The two cruciate ligament cables pass through holes drilled in femoral bone member 12 and the quadriceps muscle group cable may pass through the patella as shown in FIG. 3. The collateral ligament cables and the muscle group cables do not pass through holes and therefore the sheath ends must be secured by sheath securing posts 62. These posts 62 serve the same purpose as the holes, in that they provide a narrow passage for the cable 44 but secure the end of the sheath 46. The posts 62 are secured to the surface of femoral bone member 12 by screw threads on the bottom of the post 62 or by suitable adhesives.

In operation, each load cell such as load cell 34c is initially "set up" for two effects. Spring 38c is used to simulate the tension/elongation characteristics of the components, which is the characteristic of the component with respect to the degree of elongation resulting from applied tension. This is accomplished by selecting the spring constant such that the spring reacts to the externally applied force by appropriately regulating the degree of displacement of the joint, which in turn determines the amount of tension in cable 44c. Calibration also includes consideration of the strength and elongation characteristics of the cables, which have previously been stabilized by pretensioning. Adjustment nut 42c moves axially along threaded rod 36c, moving load cell 34c to a point where it imparts to cable 44c the amount of tension which is needed to simulate the resting tension in the PCL appropriate to the desired test pathology conditions. The resting tension is that tension which is present when the knee is at a position with no external force applied to it. This can mean putting the PCL under any degree of tension, or may involve removing all tension to simulate the loss of function of the ligament. The load cell reading (in units of Newtons or equivalent units) is determined at this point. The remaining load cells for the other ligaments and muscle groups are similarly calibrated and adjusted.

As used herein, "externally applied force which affects the knee" means any type of externally applied load, blow, trauma, stress, impact or other force, whether such force is classified as static, dynamic or impact. "Applied to the device" means applied directly to the device, as well as applied to orthopedic appliances which are mounted on the device for testing, or to extensions of the device, such as a simulated torso attached to the device. In the method of this invention, a force (such as a static load or traumatic impact) of predetermined direction and strength is applied to a predetermined point on the device. The force may be applied in a straight line or rotationally, and may be applied from an anterior, posterior, lateral, medial or oblique direction. The point of application may be on the knee joint itself; at a point along the femoral bone member 12, tibial bone member 14, fibular bone member 15, foot and ankle unit 16 or pelvis member 82; to a brace or other orthopedic appliance mounted on the device; or to an extension of the device such as a simulated pelvis or torso. One could, for instance, simulate the impact of a leg tackle to a runner in football or the impact to a vehicle occupant's knee in a automobile accident. The force will cause a differential stress in each of the cables, with the differential stress being defined as the stress imparted by the force and not already present in the cable from the set up procedures. While some differential stresses may be negative or "subtractive", in that they move the knee in a manner which reduces the stress in a particular cable, the differential stresses of medical and analytical interest are usually the positive or "additive" stresses, which increase the tension in a cable. With the proper selection of the load cell indicator and set up neutral, negative and positive differential stresses can be recorded. Usually the cable stress is transmitted from the load cell to a permanent recording means, such as a moving paper strip chart, which can be calibrated and operated to show the instantaneous stress as the stress rises to a maximum and then declines after the impact. Rate of stress application to a cable can thus be readily determined, as well as maximum stress imparted and duration of maximum stress. One could also determine other stress-related functions such as the duration of time that a cable is stressed beyond a particular predetermined value. This latter is important in determining whether a test trauma would actually have ruptured a human ligament or muscle, since the normal rupture stresses for the ligaments and muscles are known. Further, all such imparted stresses, including the instantaneous values, can be passed from the load cell to computerized equipment which can be programmed to record instantaneous and maximum values and time durations and then store and use such values to compare stresses in the different principal ligaments and muscle groups, compare stresses caused by different types of blows and so forth.

The bone members 12, 14 and 15 in the embodiment shown are formed from cast aluminum. The particular material used is not critical, as long as it generally simulates the physical characteristics of human bone.

The entire structure is supported by foot and ankle unit 16, which simulates both the movements and limits of movement of the human foot and ankle. Unit 16 consists of a generally foot-like base 64 having upwardly projecting lugs 66 thereon toward the "ankle" end. The ankle portion 68 is attached through section 70 to the distal ends of tibial bone member 14 and fibular bone member 15. In the embodiment shown the section 70 is simply a cast extension of bone member 14 which is secured by bolts to bracket 72. Bracket 72 is pivotally mounted through bolt 74 to a square bar 76 which in turn is pivotally mounted between lugs 66 by bolt 78 threaded through bar 76. The bolts 74 and 78 can be nuts or other suitable means be tightened to hold the leg member structures at any desired stable angle. The foot unit 16 can be made of the same material as the leg members 12 and 14 or of other suitable materials as desired. The foot unit 16 can also be fitted with various types of shoes, which allows the researcher to study the effects of knee trauma under different shoe/ground surface situations.

Figure 8:
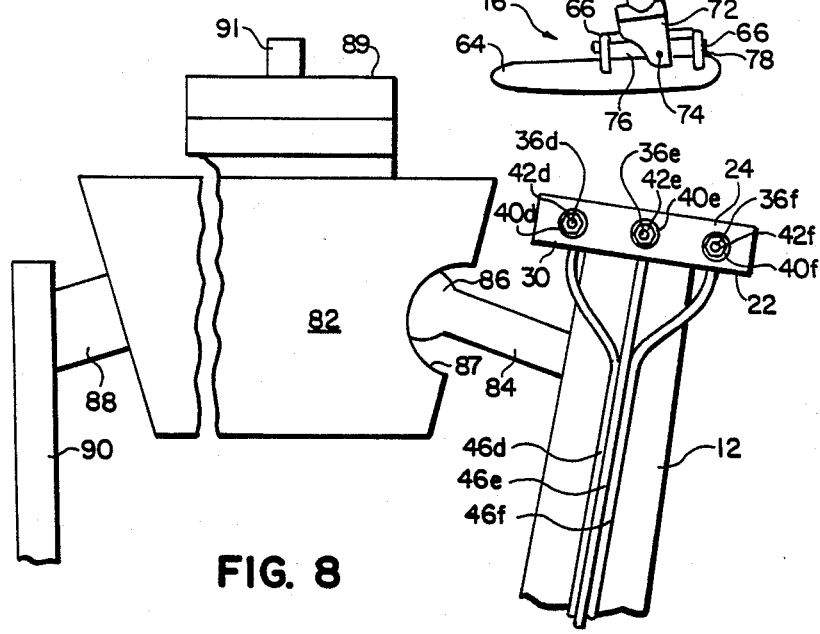
FIG. 8 is a partial plan view showing the simulated pelvis, weight adjustment and self-stabilizing elements of the device of this invention.

An optional addition to the device is shown in FIG. 8, which depicts the top of femoral bone member 12 and an end view of the load cell structure 22. The femoral bone member 12 can be attached to pelvis member 82 by means of strut 84 and ball 86 fitted into socket 87, to simulate the rotation of the hip. Pelvis member 82 is capable of holding weights 89 (mounted on rod 91) which can be used to simulate the upper body weight of a person. The opposite side of the pelvis member 82 is supported by simple strut 88 and stanchion 90.

In order to test the accuracy of this method and device in accurately simulating the effects of loading and trauma on the principal components of the human knee, comparative tests were run by applying equivalent loads and traumas to the device and to recently amputated cadaver legs. The various elements of the cadaver legs were instrumented such that the stresses imparted could be directly measured. Equivalent loads and traumas were then applied to the device of this invention and the cadaver legs. The readings obtained with the present device correlated extremely well with the readings from the cadaver legs, with differences of less than 1%. Thus, by using the method defined herein, one can obtain data from an anthropomorphic device of this invention to make accurate assessment of the response of the human knee to various types of loads and traumas, allowing accurate predictions as to the type, extent and severity of ligament, muscle, patella and menisci injury which will be sustained. The data also permit braces and other orthopedic devices to be properly designed for functional, post-operative or prophylactic purposes. One also has an accurate and thorough method of teaching and training medical and emergency personnel to become familiar with the types of injuries which can occur, so that they will readily recognize such injuries in the field.

The method and devices of this invention can be used to provide response data for many knee environments. For instance, one could encase the bone members 12, 14 and 15, including the various cables and sheaths, in a polymeric or similar material intended to simulate the mass of the leg muscles (with if desired a simulated skin covering). Measurements made of loads or traumas with such "muscle" encasing (shown in phantom at 80) will allow the experimenter to determine to what extent muscle mass can dissipate the force of a blow and reduce differential stress on the ligaments and knee muscles. The device with the muscle-and-skin covering is valuable for testing of braces and other orthopedic devices for the knee, for the results are reproducible and consistent, and the effects of the brace-to-skin interface and load dissipation can be determined.

It will be evident that there are numerous embodiments of the method and devices of this invention which are not illustrated but which are clearly within the scope and spirit of the invention. The above description is therefore intended to be exemplary only and the limits of the invention are to be determined solely from the appended claims.

We claim:

1. A method for obtaining quantitative data on the response of a human limb joint having (i) bones and (ii) other components including ligaments, muscles, patella and menisci to externally applied forces affecting the human joint, which method comprises:
   a. having an anthropomorphic device which comprises bone member means shaped so as to replicate the shape and contours of an actual human bone for simulating the configuration of the actual bones of a human limb joint at the region of the human joint including menisci, patella and condyles corresponding to those found in an actual human joint; component means cooperating with said bone means for simulating the configuration of at least one of the components of the human joint; and load determining means attached to said component means for causing a force response therein that replicates the force responses of the human joint component that is simulated to a movement of the actual human joint;
   b. calibrating the force response of said load determining means to simulate predetermined stiffness characteristics of the human joint;
   c. determining from each applicable load determining means the quantitative response of said load determining means when said anthropomorphic device is subjected to externally applied force; and
   d. determining from said response to the effect on the equivalent component in the human joint resulting from said force.

2. A method as in claim 1 for obtaining quantitative data on the response to externally applied forces of individual components related to a human knee joint having bones and other components including ligaments, muscles, patella and menisci, which method comprises:
   a. having an anthropomorphic device which comprises bone member means shaped so as to replicate the shape and contours of an actual human bone for simulating the configuration of the actual femur, tibia and fibula of a human knee joint at the region of the knee joint including menisci, patella and condyles corresponding to those found in an actual human knee joint; component means cooperating with said bone means for simulating the configuration of principal components related to the knee; and load determining means attached to said component means for causing a force response therein that replicates the force response of the principal components of the actual human knee joint to movement;

b. calibrating said load determining means to simulate predetermined stiffness characteristics of the human knee;

c. determining from said load determining means the quantitative response of said component means when said anthropomorphic device is subjected to externally applied force; and d. determining from said response the effect on the equivalent components in the human knee joint resulting from said force.

3. A method as in claim 1 wherein said component means comprises a cable subject to tension and elongation, said load determining means comprises a load cell which indicates the tension in said cable, calibration comprises selecting spring means to simulate to tension-/elongation characteristics of the equivalent component and adjusting the tension in said cable to a predetermined value representing the resting tension of the component, said external force induces a different tension in said cable, and said response is determined by observing the difference in the tensions before and after imposition of said force.

4. A method as in claim 3 wherein said tension/elongation effects in said cable are directly representative of the tension/elongation effects present in a human knee component under equivalent force conditions.

5. A method as in claim 1 wherein the principal components for which said effects are determined from said responses are related to the knee and are selected from the group consisting of the anterior cruciate ligament, the posterior cruciate ligament, the medial collateral ligament, the lateral collateral ligament, the hamstring muscles, the quadriceps muscles, the patella or the menisci.

6. An anthropomorphic device simulating the knee portion of the human leg in order that quantitative trauma-induced stresses in knee components can be observed, which device comprises:

a. at least two rigid life like bone members shaped so as to replicate the shape and contours of an actual knee, the first incorporating the general shape of the distal end of the human femur and the second incorporating the general shape of the proximal ends of the human tibia and fibula, the bone members being aligned endwise in the configuration of the actual femur, tibia and fibula of a person's knee and together simulating a human knee including menisci, patella and condyles corresponding to those of an actual human knee;

b. a plurality of cooperating pairs of cables and sheaths, each cable representing one of the group of ligament and the muscle components relating to the human knee and being slidably encased in the cooperating sheath for a portion of its length, with one end of each cable and sheath pair being operably attached to a load cell, the end of each cable distal to the load cell extending outwardly from the distal end of the sheath;

c. The distal end of the sheath being secured to a first femur-distal-end-shaped one of the bone members at a point such that the cable exits from its cooperating sheath at a point equivalent to where the one component which the cable represents would be attached or adjacent to the human femur, and the distal end of the cable being fixed to another one of the tibia-roximal-end-shaped or fibula-proximal-end shaped bone members at a point where one component would be attached to the human tibia or fibula;

d. means for calibrating the tension/elongation characteristics in each of the cable and sheath pairs to simulate predetermined stiffness and displacement characteristics of the human knee;

e. means for calibrating each of the cable and sheath pairs to simulate predetermined resting tension characteristics of the applicable individual one component related to the human knee; and f. means for determining from each load cell the differential tension imposed on the cable when the simulated knee is subjected to external traumatic force, with the differential tension being related to stress in said one component in a human knee joint resulting from said force and from which accurate analysis of the response of said one component of the knee to such force can be obtained.

7. A device as in claim 6 where said one component represented is one of the group of the anterior cruciate ligament, the posterior cruciate ligament, the medial collateral ligament, the lateral collateral ligament, the hamstring muscles, and the quadriceps muscles.

8. A device as in claim 6 wherein a plurality of said ones of the ligament and muscle components are represented simultaneously.

9. A device as in claim 6 wherein all the principal ones of the ligament and muscle components are represented simultaneously.

10. The device as in claim 6 wherein in said calibrating means (d) and (e) comprise:

a. a frame having two ends, one proximal to said bone members and one distal to said bone members, each end with a opening therethrough, said load cell being positioned between said ends;

b. said cable being passed through the opening in said proximal end of said frame and operably attached to said load cell to transmit stresses to be detected and indicated by said cell, and said sheath being butted against said proximal end of said frame surrounding the entrance to said opening;

c. a threaded rod extending upwardly from the end of said load cell opposite to the cable attachment end, with said rod extending through the opening in said distal end of said frame, and moveably secured in said frame by a nut threaded over the threaded portion of said rod extending outwardly from said opening;

d. a compression spring mounted between said nut and the distal end of said frame and bearing against the underside of said nut and the surface of said distal end surrounding the exit of said opening such that movement of said nut along said threaded rod will cause said load cell to move axially of said cable and rod within said frame imparting tension to said cable which simulates the resting tension of such component in said cable because of the anchoring of said cable and sheath at their respective ends; and e. said compression spring having a spring constant which simulates the tension/elongation characteristics of said component in said cable.

11. A device as in claim 7 wherein said cable represents the anterior cruciate ligament and its distal end passes through an opening in the distal end of the femoral bone member and emerges at a point adjacent the intercondylar notch at a point equivalent to the posterior point of attachment of the human anterior cruciate ligament, passes through intercondylar notch and is attached to the proximal end of said tibial bone member at a anterior point equivalent to the point at which the human anterior cruciate ligament would be attached to the human tibia.

12. A device as in claim 7 wherein said cable represents the posterior cruciate ligament and its distal end passes through an opening in the distal end of the femoral bone member and emerges at a point adjacent the intercondylar notch at a point equivalent to the anterior point of attachment of the human posterior cruciate ligament, passes through intercondylar notch and is attached to the proximal end of said tibial bone member at a posterior point equivalent to the point at which the human posterior cruciate ligament would be attached to the human tibia.

13. A device as in claim 7 wherein said cable represents the lateral collateral ligament and passes through a sheath securing device mounted on the lateral side of the distal end of said femoral bone member at a point equivalent to where a human lateral collateral ligament would be attached to the femur, and said distal end of said cable is secured to the lateral side of said tibial bone member at a point equivalent to where the human lateral collateral ligament would be attached to the fibula.

14. A device as in claim 7 wherein said cable represents the medial collateral ligament and passes through a sheath securing device mounted on the medial side of the distal end of said femoral bone member at a point equivalent to where a human medial collateral ligament would be attached to the femur, and said distal end of said cable is secured to the medial side of said tibial bone member at a point equivalent to where the human medial collateral ligament would be attached to the tibia.

15. A device as in claim 7 wherein said cable represents the quadriceps muscle group and passes through a sheath securing device mounted on the anterior surface of the distal end of said femoral bone member at a point equivalent to where a human patella would be adjacent to the femur, and said distal end of said cable is secured to the anterior surface of said tibial bone member at a point equivalent to where the human quadriceps muscle group would be attached to the tibia.

16. A device as in claim 15 wherein said cable passes through a member simulating the human patella.

17. A device as in claim 7 wherein said cable represents the hamstrings muscle group and passes through a sheath securing device mounted on the posterior surface of the distal end of said femoral bone member and said distal end of said cable is secured to the posterior surface of said tibial bone member at a point equivalent to where the human hamstrings muscle group would be attached to the tibia.

18. A device as in claim 7 wherein said bone members extend upwardly from a supporting foot member, said foot member being attached to the distal end of said second bone member.

19. A device as in claim 18 wherein said foot member simulates the motions and limitations on motion of the human foot and ankle.

20. A device as in claim 19 wherein said second bone member and said foot support member are rotatably attached by attachment means which can be secured to maintain said tibial bone member at a given angle relative to said foot member.

21. A device as in claim 7 wherein said load cells are contained in a structure mounted on the proximal end of said first bone member.

22. A device as in claim 7 wherein said load cells are capable of measuring and indicating differential stresses in said cables of at least 0 to 2000N.

23. A device as in claim 22 wherein said load cells are capable of measuring and indicating differential stresses in said cables of 0 to 4000N.

24. A method for determining the stresses which will occur in at least one of the principal components of the human knee which comprises subjecting the device of claim 7 to an externally applied force affecting the knee and measuring through said load cells the stress which occurs in a cable which represents said component.

25. A method as in claim 24 wherein the stresses caused by sad externally applied force in a plurality of cables representing a plurality of components are measured simultaneously.

26. A method as in claim 25 wherein said components are selected from the group consisting of the anterior cruciate ligament, the posterior cruciate ligament, the lateral collateral ligament, the medial collateral ligament, the quadriceps muscle group, the hamstrings muscle group, the patella and the menisci.

* * * * *

UNITED STATES PATENT AND TRADEMARK OFFICE

Certificate

Patent No. 4,850,877

Patented: July 25, 1989

On petition requesting issuance of a cetificate for correction of inventorship pursuant to USC 256, it has been found that the above-identified patent, through error and without any deceptive intent, improperly sets forth the inventorship. Accordingly, it is hereby certified that the correct inventorship of this patent is:
Jeffery T. Mason, Escondido, Calif., Patrick W. Cawley, San Diego, Calif., Bradley R. Mason, Carlsbad, Calif., E. Paul France, Murray, Utah.

Signed and Sealed this Sixth Day of March, 1990.

RICHARD APLEY

*Supervisory Patent Examiner*
*Art Unit 332*